United States Patent

Sasaki et al.

[11] Patent Number: 4,908,420
[45] Date of Patent: Mar. 13, 1990

[54] METHOD FOR PREPARING RESIN HAVING LIGHT COLOR

[75] Inventors: Makoto Sasaki, Yokohama; Yukio Kobayashi; Shozo Tsuchiya, both of Tokyo, all of Japan

[73] Assignee: Nippon Oil Company, Ltd., Tokyo, Japan

[21] Appl. No.: 383,007

[22] Filed: Jul. 21, 1989

[30] Foreign Application Priority Data

Jul. 27, 1988 [JP] Japan .................. 63-185427

[51] Int. Cl.$^4$ .................. C08F 32/04; C08F 32/08
[52] U.S. Cl. .................. 526/76; 526/75; 526/237; 526/280; 526/281; 526/282; 526/283; 526/290; 585/251; 585/271
[58] Field of Search .................. 526/75, 76, 77, 237, 526/281, 282, 283, 290, 280; 585/251, 271

[56] References Cited

U.S. PATENT DOCUMENTS

| | | | |
|---|---|---|---|
| 3,629,221 | 12/1971 | Arakawa et al. .................. | 526/75 |
| 3,784,481 | 1/1974 | Lassau et al. .................. | 585/271 X |
| 4,204,081 | 5/1980 | Menapace .................. | 585/271 X |
| 4,533,700 | 8/1985 | Mizui et al. .................. | 526/283 X |

Primary Examiner—Joseph L. Schofer
Assistant Examiner—F. M. Teskin
Attorney, Agent, or Firm—Majestic, Parsons, Siebert & Hsue

[57] ABSTRACT

A method for preparing a resin having light color comprises the steps of: hydrogenating a compound represented by the formula (1)

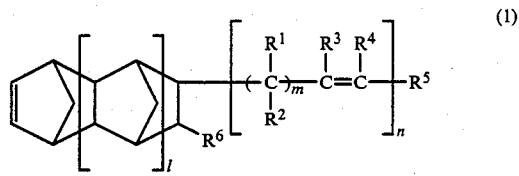

(1)

wherein l, m and n are integers of $0 \leq l \leq 3$, $0 \leq m \leq 8$ and $1 \leq n \leq 3$, respectively, and $R^1$ and $R^6$ each represent a hydrogen atom or a hydrocarbon residue having 1 to 3 carbon atoms, with or without $R^5$ and $R^6$ forming a ring, in the presence of a Ziegler catalyst containing a transition metal compound of the groups IV to VI of the Periodic Table and an organometallic compound of the groups I to III of the Periodic Table in combination to obtain a norbornene compound represented by the formula (2)

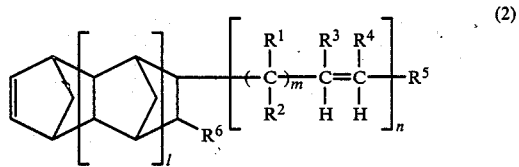

(2)

wherein l, m, n and $R^1$ and $R^6$ are the same as above; and polymerizing the norbornene compound to give the resin having light color.

17 Claims, No Drawings

METHOD FOR PREPARING RESIN HAVING LIGHT COLOR

BACKGROUND OF THE INVENTION

This invention relates to a method for preparing a light color resin using a norbornene compound.

A resin of light color is used as a tackifying resin for an adhesive or as a binder for ink or paint. Above all, in the field of a hot melt type adhesive, it is extensively used as a tackifying resin having superior quality.

As the tackifying resin for an adhesive, a petroleum resin, produced upon polymerizing fractions by-produced from the process of naphtha cracking, is generally employed. However, such a resin has a hue of yellow or brown which is markedly distinct from light color.

As one of the methods for preparing the light color resin, there are disclosed in U.S. Pat. No. 1202802 and Japanese Patent Publication No. 17075/1970 a method comprising hydrogenating a petroleum resin or a dicyclopentadiene resin. Since one of the reasons why the petroleum resin is colored resides in the presence of double bonds in the resin, these double bonds are acted upon by hydrogenation to turn the color into light color. However, elevated temperatures and pressures are necessitated in hydrogenating the resin, while the operation of the hydrogenating system is always accompanied by risk. The construction of the system is also costly.

As another method, it is also known to polymerize pure monoolefins to produce a resin of light color substantially free from double bonds. On the other hand, the light color resin of the aromatic series resin is prepared by polymerizing pure aromatic monoolefins, such as styrene or α-methylstyrene. However, the resin in its entirety is of the aromatic skeleton in this case and hence has a narrow range of compatibility with polymer components of an adhesive so that the usage and application of the resin is restricted.

Turning to a dicyclopentadiene resin, there is disclosed in Japanese Patent Publication No. 11818/1972 a method comprising hydrogenating one of two double bonds of dicyclopentadiene of the starting material in the presence of nickel or palladium catalysts to give dihydrodicyclopentadiene, which is then polymerized to produce the resin, as indicated by the following reaction schema:

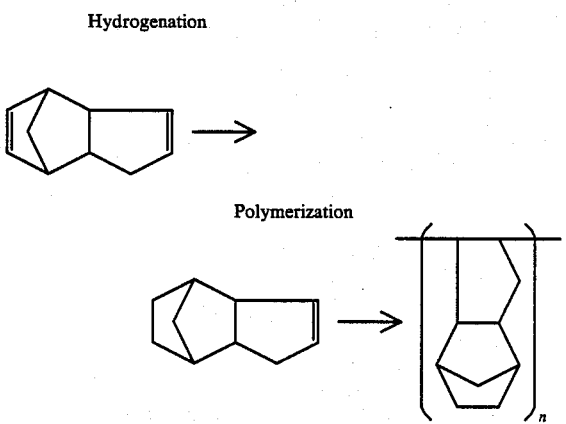

The reaction condition in this case is mild since it is not the resin but the monomer that is hydrogenated. In this reaction, the double bond of the norbornene ring is selectively hydrogenated and the double bond of the cyclopentene ring remains in the ultimately produced 9,10 dihydrodicyclopentadiene. However, the double bond of the cyclopentene ring exhibits only poor polymerizability as compared with that of the double bond of the norbornene ring, such that it is difficult to produce the resin with a high yield with the use of 9,10-dihydrodicyclopentadiene as a starting material. On the other hand, a larger amount of the polymerization catalyst need be used for producing the resin with a high yield, in which case, however, the resin is affected in hue significantly.

The norbornene compounds represented by the formula (1), described hereunder, other than dicyclopentadiene, are also not suited as the starting material for preparing the resin having light color since hydrogenation thereof in the known manner results in only the double bond of the norbornene ring being hydrogenated and the other double bonds of lower reactivity remaining unhydrogenated.

While it is thought possible to produce the resin of light color with a high yield by polymerizing a compound having the formula (2) described hereunder, containing only the double bond of the norbornene ring having higher polymerizability, such as 1,2-dihydrodicyclopentadiene represented by the following formula

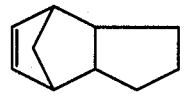

1,2-Dihydrodicyclopentadiene it is practically difficult to produce the resin with a high yield and high purity since the compound of the formula (2) is conventionally synthesized by the Diels-Alder reaction between cyclopentadiene and monoolefin, such that it is technologically impractical and undesirable to produce the compound (2) and to polymerize the compound to produce the resin having light color.

SUMMARY OF THE INVENTION

It is a principal object of the present invention to provide a method for preparing a resin having light color at a high yield by a simplified manufacturing process.

It is another object of the present invention to provide a simplified method for preparing a resin having light color which is useful as the tackifying resin for an adhesive or as a binder for ink or paint.

These and other objects of the invention will become apparent from the following description.

The present inventors have conducted eager researches for overcoming the aforementioned problems of the prior art methods and found that the resin of light color may can easily be prepared with a high yield by a simplified process comprising selectively and partially hydrogenating a diene monomer having a double bond of the norbornene ring in the presence of a specific catalyst to produce a monomer containing only a highly polymerizable double bond of the norbornene ring with a high yield and purity and polymerizing the monomer.

Thus, the present invention provides a method for preparing a resin having light color comprising the steps of:

hydrogenating a compound represented by the formula (1)

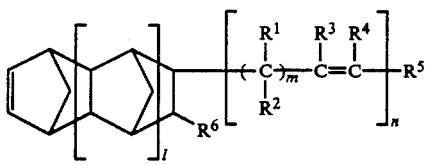
(1)

wherein l, m and n are integers of $0 \leq l \leq 3$, $0 \leq m \leq 8$ and $1 \leq n \leq 3$, respectively, and $R^1$ to $R^6$ each represent a hydrogen atom or a hydrocarbon residue having 1 to 3 carbon atoms, with or without $R^5$ and $R^6$ forming a ring, in the presence of a Ziegler catalyst containing a transition metal compound of the groups IV to VI of the Periodic Table and an organometallic compound of the groups I to III of the Periodic Table in combination to obtain a norbornene compound represented by the formula (2)

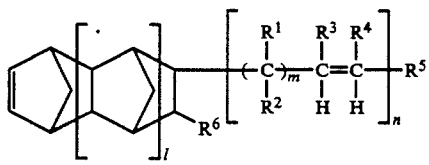
(2)

wherein l, m, n and $R^6$ are the same as above; and polymerizing the norbornene compound to give the resin having light color.

The present invention will be explained in more detail hereinbelow.

According to the present invention, the compound represented by the formula (1)

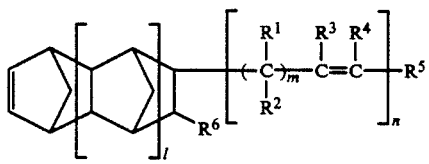
(1)

is hydrogenated in the presence of a Ziegler catalyst containing a transition metal compound of the groups IV to VI of the Periodic Table and an organometallic compound of the groups I to III of the Periodic Table in combination to produce the compound represented by the formula (2)

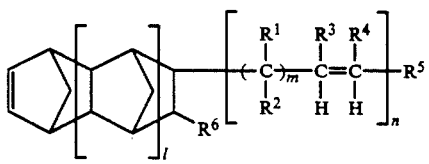
(2)

with a high purity. In the above formulas, l, m and n stand for integers of $0 \leq l \leq 3$, $0 \leq m \leq 8$ and $1 \leq n \leq 3$ and $R^1$ to $R^6$ each stand for a hydrogen atom or a hydrocarbon residue having 1 to 3 carbon atoms, with or without $R^5$ and $R^6$ forming a ring. In case of $l > 3$, $m > 8$ or $n > 3$, manufacture is rendered to be inconveniently difficult.

Similarly, with the compounds $R^1$ to $R^6$ containing hydrocarbon residues having not less than four carbon atoms, manufacture is rendered to be inconveniently difficult.

Examples of the compounds employed in the present invention and represented by the formula (1) include dicyclopentadiene, tricyclopentadiene, tetracyclopentadiene, 5-vinylbicyclo[2. 2. 1]hept-2-ene, 2-vinyl-1, 4, 5, 8-dimethano-1, 2, 3, 4, 4a, 5, 8, 8a-octahydronaphthalene, 5-propenylbicyclo[2. 2. 1]hept-2-ene, 2-propenyl-1, 4, 5, 8-dimethano-1, 2, 3, 4, 4a, 5, 8, 8a-octahydronaphthalene, 5-isopropenylbicyclo2. 2. 1]hept-2-ene, 2-isopropenyl-1, 4, 5, 8-dimethano-1, 2, 3, 4, 4a, 5, 8, 8a-octahydronaphthalene, 5-methyl-6-vinylbicyclo[2. 2. 1]hept-2-ene, 2-methyl-3-vinyl-1, 4, 5, 8-dimethano-1, 2, 3, 4, 4a, 5, 8, 8a-octahydronaphthalene, 5-(1-butenyl)-bicyclo[2. 2. 1] hept-2-ene, 2-(1-butenyl)-1, 4, 5, 8-dimethano-1, 2, 3, 4, 4a, 5, 8, 8a-octahydronaphthalene, 5-(2-butenyl)-bicyclo[2. 2. 1]hept-2-ene, 2-(2-butenyl)-1, 4, 5, 8-dimethano-1, 2, 3, 4, 4a, 5, 8, 8a-octahydronaphthalene, 5-methyl-6-propenylbicyclo[2. 2. 1]hept-2-ene, 2-methyl-3-propenyl-1, 4, 5, 8-dimethano-1, 2, 3, 4, 4a, 5, 8, 8a-octahydronaphthalene, 1, 4-methano-1, 4, 4a, 7, 8, 8a-hexahydronaphthalene, 1, 4-methano-1, 4, 4a, 5, 8, 8a-hexahydronaphthalene, 1, 4, 5, 10-dimethano-1, 4, 4a, 5, 5a, 8, 9, 9a, 10, 10a-decahydroanthracene and 1, 4, 5, 10-dimetahano-1, 4, 4a, 5, 5a, 6, 9, 9a, 10, 10a-decahydroanthracene.

Among these, dicyclopentadiene may be produced from by-product oil from naphtha cracking, whereas the remaining compounds may be synthesized easily by the Diels-Alder reaction between polyene and cyclopentadiene obtained from the by-product oil.

Among these compounds, dicyclopentadiene, 5-vinylbicyclo[2. 2. 1]hept-2-ene, 2-vinyl-1, 4, 5, 8-dimethano-1, 2, 3, 4, 4a, 5, 8, 8a-octahydronaphthalene, may be obtained easily on industrial scale.

The Ziegler catalyst employed in the hydrogenating reaction of the present invention is a system consisting of the combination of transition metal compounds of the groups IV to VI of the Periodic Table and organometallic compounds of the groups I to III of the Periodic Table. The transition metal compounds are, for example, those having the formula $M(OR)nXz-n$, wherein M stands for a transition metal, such as Ti, Zr, Hf, V, Cr, Mo or W and preferably Ti, Zr, Hf or V. R stands for an aliphatic or alicyclic hydrocarbon residue having 1 to 6 carbon atoms, X stands for a halogen atom, preferably C , Br or I, n stands for an integer of 0, 1, 2, 3 or 4 and Z stands for the number of valency for M. More specifically, the transition metal compounds may include, for example, alkoxides such as titanium ethoxide, titanium isopropoxide, titanium butoxide, zirconium ethoxide, zirconium isopropoxide, zirconium butoxide, hafnium ethoxide, hafnium butoxide, vanadium ethoxide, vanadium isopropoxide, vanadium butoxide, vanadyl ethoxide, vanadyl isopropoxide or vanadyl butoxide and halogenides such as titanium trichloride, titanium tribromide, titanium triiodide, titanium tetrachloride, titanium tetrabromide, titanium tetraiodide, zirconium tetrachloride, zirconium tetrabromide, zirconium tetraiodide, hafnium tetrachloride, hafnium tetrabromide, vanadium chloride, vanadyl tetrabromide, vanadyl chloride, vanadyl bromide, vanadyl monoethoxydichloride or vanadyl diethoxymonochloride. Acetylacetonates such as titanium acetylacetonate, zirconium acetylacetonate, hafnium acetylacetonate, vanadium acetylacetonate or vanadyl acetylacetonate, carbonyl compounds such as vanadium hexacarbonyl, cyclopentadienyl metal carbonyls such as biscyclopentadienyl titanium dicarbonyl or cyclopentadienyl vanadium tetracarbonyl, biscyclopentadienyl compounds such as biscyclopentadienyl titanium dichloride, biscyclopentadienyl vanadium dichloride or biscyclopentadienyl titanium dimers, or alkyl complexes such as methyl titanium trichloride, may also be used as the transition metal compounds.

These transition metal compounds may also be supported on suitable carriers, such as, for example, $Al_2O_3$, MgO, $MgCl_2$ or $SiO_2$ The carriers may preferably be treated in advance with electron donors.

The organometallic compounds of the groups I to III may be enumerated, for example by organo-alkali metal compounds such as methyl lithium, ethyl lithium, n-propyl lithium, n-butyl lithium, sec-butyl lithium, cyclohexyl lithium, phenyl lithium, benzyl lithium, phenyl sodium, benzyl sodium, naphthalene sodium, triphenyl methyl sodium, phenyl potassium, butadiene potassium, styrene potassium or naphthalene potassium, organoalkaline earth metal compounds such as methylmagnesium chloride, ethylmagnesium bromide, n-butylmagnesium chloride, butylmagnesium iodide, phenylmagnesium chloride, vinylmagnesium chloride, allylmagnesium chloride, diethyl magnesium, dibutyl magnesium, methylzinc iodide, ethylzinc iodide, n-propylzinc iodide, dimethyl zinc, diethyl zinc, dibutyl zinc, dimethyl cadmium, diethyl cadmium, dibutyl cadmium or diphenyl cadmium, and organometallic compounds of the metals of the group III, such as trimethyl aluminum, triethyl aluminum, triisobutyl aluminum, tricyclohexyl aluminum, diethylaluminum chloride, ethylaluminum sesquichloride, ethylaluminum dichloride or diethylethoxy aluminum.

The reaction of the present invention may be carried out not only in the solvent-free state but in the presence of solvents not interfering with the reaction. As these solvents, for example, hydrocarbon solvents such as hexane, heptane, octane, cyclohexane, decalin, benzene, toluene or xylene or ethers such as diethyl ether, diisopropyl ether, dibutyl ether, tetrahydrofuran, tetrahydropyran, diphenyl ether, glyme or diglyme, may be employed. Depending on the kinds of the organometal compounds employed, halogenated hydrocarbons, such as chlorobenzene, may also be employed as the solvents. Although indene or norbornadiene may also be used as the solvents, these may rather be used as ligands for improving the selectivity of tee present reaction.

The concentration of the substrate of the present reaction may be selected arbitrarily from the order of magnitude of 0.1 mol/lit. to the value corresponding to the solvent-free state.

The transition metal compound used as the catalyst may be employed at a molar ratio relative to the compound represented by the formula (1) in the range of from 0.0001:1 to 0.005:1. Although it is seemingly preferred to use a larger amount of the compound, such is not desirable inasmuch as heat evolution is increased so that the reaction conditions become difficult to control and costly post-processing need be performed after completion of the reaction. The transition metal compound and the organometal compound are employed in a relative molar ratio of 1:3 to 1:100 and preferably 1:5 to 1:20.

It is preferred to use hydrogen of high purity, while the presence of oxidating impurities, such as oxygen, above all, is not desired. The pressure of hydrogen employed in the reaction may be a subatmospheric pressure but may preferably be 0 to 100 $kg/cm^2G$ and more preferably 1 to 20 $kg/cm^2G$.

The reaction temperature is in the range of $-30°$ to 200° C. and preferably 0° to 100° C.

The end point of the reaction may be selected arbitrarily. In general, the compound represented by the formula (1) is difficult to isolate from the norbornene compound represented by the formula (2) since they differ from each other only by the presence or absence of two hydrogen atoms. Thus, one may proceed in such a fashion that the conversion rate be raised to as high a value as possible so that the amount of the compound of the formula (1) is decreased and substantially only the norbornene compound of the formula (2) is effectively obtained. Alternatively, the reaction may be terminated at an arbitrarily selected conversion rate of, for example, 80%, and the reaction product may be used as a mixture of the compounds (1) and (2). Still altenatively, the unreacted feedstock may be converted into other compounds by some or other methods.

The norbornene compound of the formula (2) is then polymerized to a resin having light color. Although the method of polymerization may be by radical polymerization or ionic polymerization, cationic polymerization is most preferred.

As the cationic catalysts, Friedel-Crafts catalysts, such as $AlCl_3$, $AlRCl_2$, $AlR_2Cl$, $AlR_3$, R being an alkyl group, $BF_3$, $SnCl_4$, $FeCl_3$, $AlBr_3$ or complexes thereof with phenols, alcohols, esters or ethers, may be employed. Of these, aluminum or boron type catalysts are of higher catalytic activity and therefore preferred. Co-catalysts such as $(CH_3)_3CCl$ or $C_6H_5CH_2Cl$ may also be employed.

The catalyst may be used in an amount of 0.01 to 10 mol.% and preferably 0.05 to 8 mol. % based on the norbornene compound of the formula (2). With the amount of the catalyst less than 0.01 mol. %, it becomes difficult to produce the resin with a high yield. With the amount of the catalyst in excess of 10 mol%, on the other hand, the resin is affected in hue significantly.

The polymerization temperature is $-100°$ to 150° C. and preferably $-70°$ to 130° C., while the polymerization period is preferably 30 minutes to 10 hours. With the polymerization temperature lower than $-100°$ C., the polymerization process becomes difficult to control industrially. On the other hand, with the polymerization temperature in excess of 150° C, the resin is affected in hue abruptly.

As the polymerization solvents, hydrocarbon or chlorine solvents may be employed. The hydrocarbon solvents may be enumerated by hexane, heptane, cyclohexane, methyl cyclohexane, benzene, toluene or xylene, whereas the chlorine solvents may be enumerated by dichloromethane or dichloroethane.

After termination of the reaction, the reaction mass may be neutralized by any known methods with the use of water, alcohol or alkali.

It is also possible to copolymerize other olefins so long as they are employed in an amount which does not affect the resin hue or which does not lower the properties of the resin employed as the tackyfying resin. Monoolefins may include butene, pentene, hexene, heptene, octene, cyclohexene, styrene, α-methylstyrene or indene, while diolefins may include butadiene, isoprene, piperylene, vinylcyclohexene, pinene or dicyclopentadiene and mixed olefins may include $C_5$ or $C_9$ fractions obtained from naphtha cracking. Of these, styrene and α-methylstyrene are preferred in view of reactivity, resin hue and compatibility when the resin is used as the tackyfying resin.

Turning to the amount of the other olefins, not more than 20 parts by weight to 100 parts by weight of the norbornene compound of the formula (2) are preferred when the other olefins are diolefins or mixed olefins, while not more than 200 parts by weight to 100 parts by weight of the norbornene compound of the formula (2) are preferred when the other olefins are monoolefins.

The resin thus prepared has a softening point of 30 to 180° C, molecular weight of 300 to 5000 and the bromine value of not more than 15. The hue is light yellow or pale white.

The resin prepared by the above described method exhibits superior properties when used as the tackyfying resin for the adhesive.

EXAMPLES OF THE INVENTION

The description with reference to several specific examples of the present invention is given hereinbelow. It should be noted that the scope of the invention is by no means limited to these specific examples but any other modes may be adopted insofar as they are pursuant to the object of the invention.

Experiment 1

2 mmol of titanocenedichloride, 400 cc of benzene, 184.8 g of dicyclopentadiene and 32 mmol of triethylaluminum were charged into a 2 liter autoclave which had been dried thoroughly and which had been replaced by nitrogen. The reaction was carried out with the polymerization temperature being controlled to 50° C. while hydrogen was added to the reaction system so that the pressure was maintained at 4 kg/cm$^2$ (gauge pressure). Analyses after five hours by gas chromatography revealed that the conversion rate amounted to 92.1%. After methanol was added to the reaction solution to deactivate the catalyst, distillation was carried out under reduced pressure to produce 119.0 g of 1,2-dihydrodicyclopentadiene having the purity of 97.1%. Analyses by proton NMR revealed that only the signal of unsaturated proton of norbornene could be noticed in the vicinity of 5.8 ppm (δ), whereas the signal of unsaturated proton of cyclopentene in the vicinity of 5.4 ppm (δ) could not be noticed.

Experiment 2

The reaction was carried out in the same way as in Example 1 except that the substrate was changed to 5-vinylbicyclo[2. 2. 1]hept-2-ene, 6 mmol of titanocenedichloride and 60 mmol of triethyl aluminum were charged into the autoclave, and the reaction period was set to five hours, to produce 134.7 g of 5-ethylbicyclo[2. 2. 1]hept-2-ene having the purity of 98.9%. Analyses by proton NMR revealed that only the signal of unsaturated proton of norbornene could be noticed in the vicinity of 5.8 ppm (δ) whereas the signal of unsaturated proton of vinyl in the vicinity of 5.0 ppm (δ) could not be noticed.

Comparative Experiment 1

600 g of dicyclopentadiene and 0.6 g of a palladium carbon catalyst were charged into a 2 liter autoclave which had been dried thoroughly and which had been replaced by nitrogen. The reaction was carried out with the polymerization temperature being controlled to 60° C. while hydrogen was added to the reaction system so that the pressure was maintained at 10 kg/cm$^2$ (gauge pressure). Analyses after two hours by gas chromatography revealed that the conversion rate amounted to 93.0%. After the catalyst was separated by filtration, distillation was carried out under reduced pressure to produce 438 g of 9, 10-dihydrodicyclopentadiene having the purity of 96.7%. Analyses by proton NMR revealed that only the signal of unsaturated proton of cyclopentene could be noticed in the vicinity of 5.4 ppm (δ), whereas the signal of unsaturated proton of norbornene in the vicinity of 5.8 ppm (δ) could not be noticed.

Examples 1 to 3 and Comparative Examples 1 to 3

Polymerization was carried out using the monomers and dicyclopentadiene obtained in the Experiments 1 and 2 and the Comparative Experiment 1. After neutralization with an aqueous NaOH solution, the unreacted monomer, low polymer and the solvent were removed by distillation under reduced pressure to produce each of the resins. The polymerization conditions as well as the properties of the produced resins are shown in Table 1.

TABLE 1

Preparation Conditions and Properties of Resins

| | | | Ex. 1 | Ex. 2 | Ex. 3 | Comp. Ex. 1 | Comp. Ex. 2 | Comp. Ex. 3 |
|---|---|---|---|---|---|---|---|---|
| Polymerization Conditions | Monomer | Kind | Exp. 1 | Exp. 2 | Exp. 1 | Comp. Exp. 1 | Comp. Exp. 1 | DCPD |
| | | Amount | 100 g | 100 g | 70 g | 100 g | 100 g | 100 g |
| | Comonomer | Kind | — | — | Styrene | — | — | — |
| | | Amount | — | — | 30 g | — | — | — |
| | Catalyst | Kind | AlCl$_3$ | AlCl$_3$ | AlEtCl$_2$ | AlCl$_3$ | AlCl$_3$ | AlCl$_3$ |
| | | Amount | 1.5 g | 1.5 g | 0.5 g | 1.5 g | 5 g | 1.5 g |
| | Solvent | Kind | Toluene | Toluene | Toluene/Methylcyclohexane | Toluene | Toluene | Toluene |
| | | Amount | 100 g | 100 g | 100 g | 100 g | 100 g | 100 g |
| | Polymerization Temp. °C. | | 30 | 30 | 30 | 30 | 30 | 30 |
| | Polymerization Period Hr | | 3 | 3 | 3 | 3 | 3 | 3 |
| Properties | Softening Point °C. | | 98.5 | 90.5 | 92.5 | Hardly Polymerized | 83.0 | 118.5 |
| | Bromine Value gBr/100 g | | 6.3 | 7.8 | 5.4 | | 18.3 | 62.7 |
| | Hue | | Light Yellow | Light Yellow | Pale White | | Yellowish Brown | Brown |
| Resin Yield wt % | | | 78.5 | 80.5 | 83.5 | | 72.5 | 87.5 | the vicinity of 5.8 ppm (δ), whereas the signal of unsaturated proton of cyclopentene in the vicinity of 5.4 ppm (δ) could not be noticed.

Example 4 and Comparative Examples 4 and 5

Using the resin produced in Example 3 and a commercially available resin, the properties of these resins in terms of the hot-melt pressure sensitive adhesive were appraised. The results are shown in Table 2. Test samples were prepared and tested in the following manner.

Sample Preparation 100 parts by weight of a SBS block polymer prepared by SHELL KAGAKU KK under the trade name of "CARIFLEX TR-1102", 125 parts by weight of the resins and 75 parts by weight of oil prepared by SHELL KAGAKU KK under the trade name of "SHELL-FLEX 371JY" were heat-melted and mixed at 180° C. The resulting mixtures were coated on PET films each having the thickness of 40 μm with the aid of an applicator. The thus coated films were allowed to cool to prepare test samples.

Testing of Adhesive Power (J. Dow type Rolling Tack)

The test samples were held on a test rack for measuring adhesive power set to an angle of 30°, with the coated side facing upwards. Steel balls of 1/32 inch (No.1) to 32/32 inch (No. 32) in diameter were caused to run on the test rack after an approach run of 10 cm. The number indication of the stopped ball having the maximum number was adopted as the indiciation of the initial adhesive power.

Testing of Tackifying Power (180° peeling method) 1532.

Testing of Cohesive Power (0° Holding Power Method)

Testing was conducted in accordance with JIS Z 1524.

Test samples were each stuck on a stainless steel plate over an area of 25×25 nm. With the test samples maintained upright, a load of 1 kg was applied to the samples, and the time period that elapsed until the samples slid down was measured at the atmosphere temperature of 50° C.

TABLE 2

| | Hot Melt Adhesive Test | | |
|---|---|---|---|
| Resin | Ex. 4 Resin Obtained in Ex. 3 | Comp. Ex. 4 ESCOREZ 1304 *1 | Comp. Ex. 5 ARKON M-100 *2 |
| Adhesive g/25 mm Power | 1930 | 950 | 1240 |
| Tackyfying Ball No. Power | 15 | 3> | 12 |
| Cohesive min. Power | 900 | 45 | 845 |

Note
*1 Esso Chemical Co., Ltd., C5 base Petroleum Resin
*2 Arakawa Chemical Co., Ltd., Hydrogenated Petroleum Resin It is seen from Table 1 that the resins having light color may be obtained with high yields by the method of the present invention. It is also seen from Table 2 that the resin produced exhibits superior tackyfying properties.

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method for preparing a resin having light color comprising the steps of:
hydrogenating a compound represented by the formula (1)

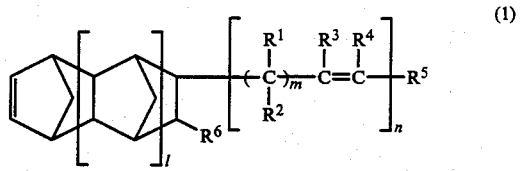

wherein l, m and n are integers of $0 \leq l \leq 3$, $0 \leq m \leq 8$ and $1 \leq n \leq 3$, respectively, and $R^1$ to $R^6$ each represent a hydrogen atom or a hydrocarbon residue having 1 to 3 carbon atoms, with or without $R^5$ and $R^6$ forming a ring, in the presence of a Ziegler catalyst containing a transition metal compound of the groups IV to VI of the Periodic Table and an organometallic compound of the groups I to III of the Periodic Table in combination to obtain a norbornene compound represented by the formula (2)

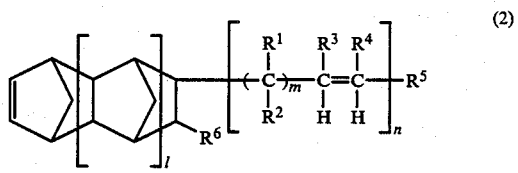

wherein l, m, n and $R^1$ to $R^6$ are the same as above; polymerizing the norbornene compound to give said resin having light color.

2. The method according to claim 1 wherein the compound represented by the formula (1) is selected from the group consisting of dicyclopentadiene, tricyclopentadiene, tetracyclopentadiene, 5-vinylbicyclo[2. 2. 1,]hept-2-ene, -vinyl-1, 4, 5, 8-dimethano-1, 2, 3, 4, 4a, 5, 8, 8a-octahydronaphthalene, 5-propenylbicyclo[2. 2. 1]hept-2-ene, 2-propenyl-1, 4, 5, 8-dimethano-1, 2, 3, 4, 4a, 5, 8, 8a-octahydronaphthalene, 5-isopropenylbicyclo[2. 2. 1]hept-2-ene, 2-isopropenyl-1, 4, 5, 8-dimethano-1, 2, 3, 4, 4a, 5, 8, 8a-octahydronaphthalene, 5-methyl-6-vinylbicyclo[2. 2. ]hept-2-ene, 2-methyl-3-vinyl-1, 4, 5, 8-dimethano-1, 2, 3, 4, 4a, 5, 8, 8a-octahydronaphthalene, 5-(1-butenyl)-bicyclo[2. 2. 1]hept-2-ene, 2-(1-butenyl)-1, 4, 5, 8-dimethano-1, 2, 3, 4, 4a, 5, 8, 8a-octahydronaphthalene, 5-(2-butenyl)-bicyclo[2. 2. 1]hept-2-ene, 2-(2-butenyl)-1, 4, 5, 8-dimethano-1, 2, 3, 4, 4a, 5, 8, 8a-octahydronaphthalene, 5-methyl-6-propenylbicyclo[2. 2. 1]hept-2-ene, 2-methyl-3-propenyl-1, 4, 5, 8-dimethano-1, 2, 3, 4, 4a, 5, 8, 8a-octahydronaphthalene, 1, 4-methano-1, 4, 4a, 7, 8, 8a-hexahydronaphthalene, 1, 4-methano-1, 4, 4a, 5, 8, 8a-hexahydronaphthalene, 1, 4, 5, 10-dimethano-1, 4, 4a, 5, 5a, 8, 9, 9a, 10, 10a-decahydroanthracene, 1, 4, 5, 10-dimetahano-1, 4, 4a, 5, 5a, 6, 9, 9a, 10, 10a-decahydroanthracene and mixtures thereof.

3. The method according to claim 1 wherein said transition metal compound has the formula $M(OR)_n X_{z-n}$ wherein M stands for a transition metal, R an aliphatic or alicyclic hydrocarbon residue having 1 to 6 carbon atoms, X a halogen atom, n an integer of from 0 to 4 and Z the number of valency for M.

4. The method according to claim 1 wherein said organometallic compound is selected from the group consisting of methyl lithium, ethyl lithium, n-propyl lithium, n-butyl lithium, sec-butyl lithium, cyclohexyl lithium, phenyl lithium, benzyl lithium, phenyl sodium, benzyl sodium, naphthalene sodium, triphenyl methyl sodium, phenyl potassium, butadiene potassium, styrene potassium, naphthalene potassium, methylmagnesium chloride, ethylmagnesium bromide, n-butylmagnesium chloride, butylmagnesium iodide, phenylmagnesium chloride, vinylmagnesium chloride, allylmagnesium chloride, diethyl magnesium, dibutyl magnesium, methylzinc iodide, ethylzinc iodide, n-propylzinc iodide, dimethyl zinc, diethyl zinc, dibutyl zinc, dimethyl cadmium, diethyl cadmium, dibutyl cadmium, diphenyl cadmium, trimethyl aluminum, triethyl aluminum, triisobutyl aluminum, tricyclohexyl aluminum, diethylaluminum chloride, ethylaluminum sesquichloride, ethylaluminum dichloride, diethylethoxy aluminum and mixtures thereof.

5. The method according to claim 1 wherein a molar ratio of said transition metal compound to the compound represented by the formula (1) is in the range of from 0.0001:1 to 0.005:1.

6. The method according to claim 1 wherein a molar ratio of said transition metal compound to said organometallic compound is in a ratio of 1:3 to 1:100.

7. The method according to claim 1 wherein said hydrogenation is carried out under a hydrogen pressure of 0 100 to kg/cm$^2$G and at a reaction temperature of $-30°$ to $200°$ C.

8. The method according to claim 1 wherein said norbornene compound represented by the formula (2) is polymerized in the presence of a Friedel-Crafts catalyst.

9. The method according to claim 1 wherein a catalyst is employed in an amount of 0.01 to 10 mol % based on said norbornene compound represented by the formula (2).

10. The method according to claim 1 wherein said polymerization is carried out at $-100°$ to $150°$ C. for 30 minutes to ten hours.

11. The method according to claim 1 wherein said norbornene compound represented by the formula (2) is co-polymerized with other olefins.

12. The method according to claim 11 wherein not more than 20 parts by weight of said other olefins selected from the group consisting of diolefins, mixed olefins and mixtures thereof are co-polymerized with 100 parts by weight of said norbornene compounds represented by the formula (2).

13. The method according to claim 12 wherein said diolefins are selected from the group consisting of butadiene, isoprene, piperylene, vinylcyclohexene, pinene, dicyclopentadiene and mixtures thereof.

14. The method according to claim 12 wherein said mixed olefins are selected from the group consisting of $C_5$ and $C_9$ fractions obtained from naphtha cracking, and mixtures thereof.

15. The method according to claim 11 wherein not more than 200 parts by weight of monoolefins are co-polymerized with 100 parts by weight of said norbornene compound represented by the formula (2).

16. The method according to claim 15 wherein said monoolefins are selected from the group consisting of butene, pentene, hexene, heptene, octene, cyclohexene, styrene, α-methylstyrene, indene and mixtures thereof.

17. The method according to claim 1 wherein said resin has a softening point of 30° to 180° C., molecular weight of 300 to 5000 and a bromine value of not higher than 15.

* * * * *

UNITED STATES PATENT AND TRADEMARK OFFICE
CERTIFICATE OF CORRECTION

PATENT NO. : 4,908,420

DATED : March 13, 1990

INVENTOR(S) : SASAKI et al

It is certified that error appears in the above-identified patent and that said Letters Patent is hereby corrected as shown below:

ON THE TITLE PAGE,
ABSTRACT [57] formula 2, replace " 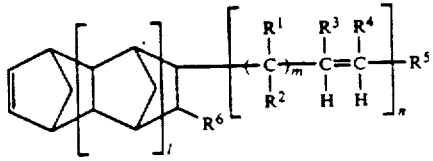 "

with -- 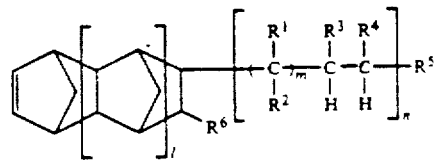 --

Column 3, lines 24-32, replace " 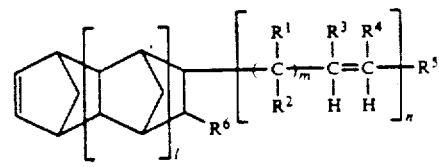 "

with -- 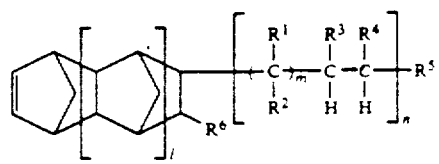 --

Column 3, line 33, insert --$R^1$ to-- before $R^6$

UNITED STATES PATENT AND TRADEMARK OFFICE
CERTIFICATE OF CORRECTION

PATENT NO. : 4,908,420
DATED : March 13, 1990
INVENTOR(S) : SASAKI et al

It is certified that error appears in the above-identified patent and that said Letters Patent is hereby corrected as shown below: continued Column 3, lines 54-61    replace " 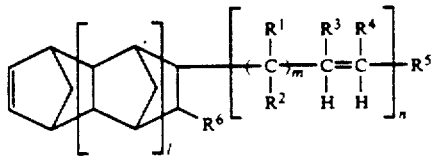 "

with -- 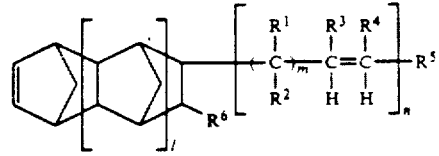 --

Column 10, lines 6-14, in Claim 1    replace " 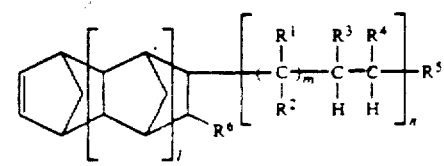 "

with -- 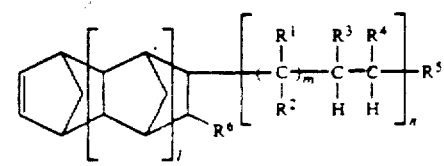 --

Signed and Sealed this

Ninth Day of July, 1991

Attest:

HARRY F. MANBECK, JR.

Attesting Officer    Commissioner of Patents and Trademarks